United States Patent
Armstrong

(10) Patent No.: US 9,753,352 B1
(45) Date of Patent: *Sep. 5, 2017

(54) HIGH DAMAGE THRESHOLD FREQUENCY CONVERSION SYSTEM

(71) Applicant: KLA-Tencor Corporation, Milpitas, CA (US)

(72) Inventor: J. Joseph Armstrong, Fremont, CA (US)

(73) Assignee: KLA-Tencor Corporation, Milpitas, CA (US)

(*) Notice: Subject to any disclaimer, the term of this patent is extended or adjusted under 35 U.S.C. 154(b) by 36 days.

This patent is subject to a terminal disclaimer.

(21) Appl. No.: 14/838,686

(22) Filed: Aug. 28, 2015

Related U.S. Application Data

(63) Continuation of application No. 14/245,020, filed on Apr. 4, 2014, which is a continuation of application
(Continued)

(51) Int. Cl.

| | |
|---|---|
| *G02F 1/35* | (2006.01) |
| *G02F 1/37* | (2006.01) |
| *G02B 27/14* | (2006.01) |
| *G02B 3/06* | (2006.01) |
| *G02B 27/00* | (2006.01) |
| *G02B 5/30* | (2006.01) |

(Continued)

(52) U.S. Cl.
CPC ....... *G02F 1/3532* (2013.01); *G01N 21/8806* (2013.01); *G01N 21/9501* (2013.01); *G02B 3/06* (2013.01); *G02B 5/3066* (2013.01); *G02B 27/0025* (2013.01); *G02B 27/141* (2013.01); *G02F 1/37* (2013.01); *H01S 3/0092* (2013.01); *G01N 2201/068* (2013.01); *G01N 2201/06113* (2013.01)

(58) Field of Classification Search
None
See application file for complete search history.

(56) References Cited

U.S. PATENT DOCUMENTS

| | | |
|---|---|---|
| 4,272,694 A | 6/1981 | Jacobs |
| 5,113,402 A | 5/1992 | Itani et al. |
| | (Continued) | |

FOREIGN PATENT DOCUMENTS

| | | |
|---|---|---|
| JP | 05-251804 A | 9/1993 |
| JP | 08-036201 A | 2/1996 |
| | (Continued) | |

*Primary Examiner* — Hemang Sanghavi
(74) *Attorney, Agent, or Firm* — Suiter Swantz pc llo

(57) ABSTRACT

The present invention includes a fundamental laser light source configured to generate fundamental wavelength laser light, a first nonlinear optical crystal configured to generate first alternate wavelength light, a second nonlinear optical crystal configured to generate second alternate wavelength light, a set of Brewster angle wavefront processing optics configured to condition the first and second alternate wavelengths of light, and a harmonic separator configured to receive the first alternate wavelength light and the second alternate wavelength light from the set of Brewster angle wavefront processing optics, the harmonic separator configured to at least partially separate the first alternate wavelength light from the second alternate wavelength light.

23 Claims, 14 Drawing Sheets

Related U.S. Application Data

No. 13/293,485, filed on Nov. 10, 2011, now Pat. No. 8,711,470.

(60) Provisional application No. 61/413,469, filed on Nov. 14, 2010.

(51) Int. Cl.
*H01S 3/00* (2006.01)
*G01N 21/95* (2006.01)
*G01N 21/88* (2006.01)

(56) References Cited

U.S. PATENT DOCUMENTS

| | | | |
|---|---|---|---|
| 5,247,389 A | 9/1993 | Beausoleil | |
| 6,229,829 B1 | 5/2001 | Yin | |
| 6,229,839 B1 | 5/2001 | Levin et al. | |
| 7,460,569 B2 * | 12/2008 | Van Saarloos | G02B 26/0875 |
| | | | 359/326 |
| 2003/0142703 A1 | 7/2003 | Gao et al. | |
| 2003/0142704 A1 | 7/2003 | Lawandy | |

FOREIGN PATENT DOCUMENTS

| | | |
|---|---|---|
| JP | 09-116219 A | 5/1997 |
| JP | 10-239724 A | 9/1998 |
| JP | 2000-338530 A | 12/2000 |
| JP | 3570656 A | 9/2004 |
| JP | 2010-027971 A | 2/2010 |
| JP | 2010-243559 A | 10/2010 |

\* cited by examiner

HIGH DAMAGE THRESHOLD FREQUENCY CONVERSION SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation patent application of United States Non-Provisional Patent Application entitled High Damage Threshold Frequency Conversion System, naming Joseph Armstrong as inventor, filed Apr. 4, 2014, Application Ser. No. 14/245,020, which is a continuation patent application of U.S. Non-Provisional Patent Application entitled High Damage Threshold Frequency Conversion System, naming Joseph Armstrong as inventor, filed Nov. 10, 2011, Application Ser. No. 13/293,485, which is a regular (non-provisional) patent application of United States Provisional Patent Application, entitled High Damage Threshold Frequency Conversion System, naming Joseph Armstrong as inventor, filed Nov. 14, 2010, Application Ser. No. 61/413,469. The above-listed patent applications are incorporated herein by reference in their entirety.

TECHNICAL FIELD

The present invention generally relates to a frequency converted light source suitable for implementation in an illuminator of a semiconductor wafer or photomask inspection system, and, more particularly, to a frequency conversion system having a high damage threshold.

BACKGROUND

As the dimensions of semiconductor devices and components continue to decrease, the demand for semiconductor wafer and photomask inspection systems exhibiting high throughput and improvements in resolution continue to increase. One manner in which higher levels of resolution are attained in semiconductor and photomask inspections systems includes the utilization of an illumination source capable of emitting shorter wavelength light.

Certain practical advantages may be achieved when illuminating a wafer or reticle with light having wavelengths at or below 400 nm. Providing suitable lasers for high quality wafer and photomask inspection systems presents a particular challenge. Conventional lasers capable of generating deep ultraviolet (DUV) light energy are typically large, expensive, and suffer from relatively short lifetimes and low average power output. In order to obtain adequate throughput and defect signal-to-noise ratio (SNR), wafer and photomask inspection systems generally require a laser based illumination source having high average power, low peak power, and relatively short wavelength.

Conventionally, the primary method for providing adequate DUV power entails converting long wavelength light to shorter wavelength light, referred to herein as "frequency conversion." It is well known in the art that frequency conversion from longer wavelength light to shorter wavelength is often accomplished utilizing one or more non-linear optical crystals. In this context, frequency conversion requires high peak power light in order to produce a nonlinear response in a given non-linear optical crystal. To increase the efficiency of this process the longer wavelength light may be generated to have high average power, short optical pulses, and may be focused into the optical crystal. The original "longer wavelength" light is commonly referred to as "fundamental light."

Generating light at wavelengths below 400 nm, and especially below 300 nm, is challenging. Light sources implemented in semiconductor inspection systems require relatively high powers, long lifetimes, and stable performance. Light sources meeting these requirements for advanced inspection techniques are nonexistent in the prior art. The lifetime, power, and stability of current DUV frequency converted lasers are generally limited by the implemented frequency conversion crystal and frequency conversion scheme. This is particularly true for non-linear conversion crystals exposed to DUV wavelengths, such as, but not limited to, 355, 266, 213, and 193 nm.

Many inspection applications require the frequency converted laser power or wavefront to remain stable over time. Due to degradation of the optical coatings, as a result of exposure to high power illumination, maintaining power and wavefront stability over time is challenging. This is especially true for optical coatings in the UV-DUV portion of the given frequency conversion system. These optical elements are typically not shifted so they must survive for the lifetime of the laser, typically greater than 10,000 hours and even 20,000 hours. Mirrors in the DUV below 350 nm are typically limited to power densities of approximately 100 W/cm$^2$, and even lower for wavelengths less than 250 nm. This constraint forces optical components such as lenses and mirrors to be placed far away from the frequency conversion crystal in order to reduce the power density on the optical coatings. In the case of UV lasers with power levels greater than 0.5W, this requirement may lead to an unrealistically large laser system.

Accordingly, it is therefore desirable to have optics in the UV-DUV portion of a frequency conversion system that can withstand very high power densities without changing over time. It is also desirable that these optics be efficient for a given wavelength range of interest, producing a minimum amount of stray light. Meeting these requirements may extend the lifetime of an implementing laser, reduce operating costs and laser maintenance time, and increase overall laser reliability.

SUMMARY

An apparatus for laser frequency conversion having high damage threshold is disclosed. In one aspect, the apparatus may include, but is not limited to, a fundamental laser light source configured to generate fundamental wavelength laser light; a first nonlinear optical crystal configured to receive fundamental laser light from the fundamental laser light source, the first nonlinear optical crystal configured to generate first alternate wavelength light by frequency converting at least a portion of the received fundamental laser light to first alternate wavelength light; a second nonlinear optical crystal configured to receive first alternate wavelength light from the first nonlinear optical crystal, the second nonlinear optical crystal configured to generate second alternate wavelength light by frequency converting at least a portion of the received first alternate wavelength light to second alternate wavelength light; a set of Brewster angle wavefront processing optics configured to receive first alternate wavelength light and second alternate wavelength light from the second nonlinear optical crystal, the set of Brewster angle wavefront processing optics further configured to condition the first alternate wavelength light and second alternate wavelength light emanating from the second nonlinear optical crystal; and a harmonic separator configured to receive the first alternate wavelength light and the second alternate wavelength light from the set of Brewster angle wavefront processing optics, the harmonic separator configured to at least partially separate the first alternate wavelength light from the second alternate wavelength light.

In another aspect, an apparatus may include, but is not limited to, a fundamental laser light source configured to generate fundamental wavelength laser light; at least one nonlinear optical crystal configured to generate alternate wavelength light by frequency converting at least a portion of received laser light to alternate wavelength light; a set of Brewster angle wavefront processing optics configured to receive fundamental wavelength light and alternate wavelength light from the nonlinear optical crystal, the set of Brewster angle wavefront processing optics further configured to condition the fundamental wavelength light and the alternate wavelength light emanating from the nonlinear optical crystal, and a harmonic separator configured to receive fundamental wavelength light and alternate wavelength light from the set of Brewster angle wavefront processing optics, the harmonic separator configured to at least partially separate the fundamental wavelength light from the alternate wavelength light.

A method for laser frequency conversion with high damage threshold is disclosed. In one aspect, the method may include, but is not limited to, providing a fundamental laser light source; generating fundamental wavelength laser light utilizing the fundamental laser light source; generating first alternate wavelength light by frequency converting at least a portion of the fundamental laser light to first alternate wavelength light utilizing a first nonlinear optical crystal; generating second alternate wavelength light by frequency converting at least a portion of the first alternate wavelength light to second alternate wavelength light utilizing a second nonlinear optical crystal; conditioning the first alternate wavelength light and second alternate wavelength light utilizing Brewster angle wavefront processing optics; and separating at least a portion of the first alternate wavelength light from the second alternate wavelength light utilizing a harmonic separator including a harmonic separation element having a first Brewster angle surface, a total internal reflection surface, and a second Brewster angle surface.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention, and, together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1 through 11, a frequency conversion system with high damage threshold is described in accordance with the present invention.

The present disclosure is directed to a system for laser frequency conversion capable of withstanding high power illumination at small wavelengths (e.g., below 400 nm). In order to produce high beam powers at wavelengths less than 400 nm, fundamental light sources combined with multiple stages of frequency conversion are typically used. Frequency conversion of continuous or quasi-continuous light often requires the light to be focused to very small spots within a utilized nonlinear crystal. Optics that are in proximity to the frequency conversion crystal, especially optics in regions where light at wavelengths of less than 400 nm is created, may suffer significant degradation to optical coatings used for anti-reflection, reflection, and harmonic separation. Typical damage thresholds for lifetimes of 10,000 hours are 30-100 watts/cm$^2$ and may be much less for wavelengths below 250 nm. A conservatively configured laser producing 1 W of power in a 1 mm diameter beam corresponds to a power density of 127 W/cm$^2$. In addition, high peak powers produced by pulsed lasers may further shorten coating lifetimes. In contrast, uncoated optics often have surface damage thresholds that approach that of the bulk material. In the UV-DUV range, this is typically many orders of magnitude greater than optical coatings.

It is an object of the present invention to provide a frequency converted laser system which operates in the absence of optical coatings. The frequency converted laser system of the present invention includes various novel optical approaches, including, but not limited to, a Brewster angle dual wavelength waveplate, Brewster angle lenses, and Brewster angle-total internal reflection (TIR) harmonic separation elements. It is further contemplated that in addition to improved damage threshold, the implementation of the various optical elements described through the present disclosure may also provide: reduced stray light with the system, 100% theoretical efficiency for the desired wavelength, and reduced system size due to the dramatic increase in damage threshold. Moreover, since no optical coatings are utilized, the system may easily be modified to work with any desired wavelength capable of transmission through glass or crystalline material.

Figure 1:
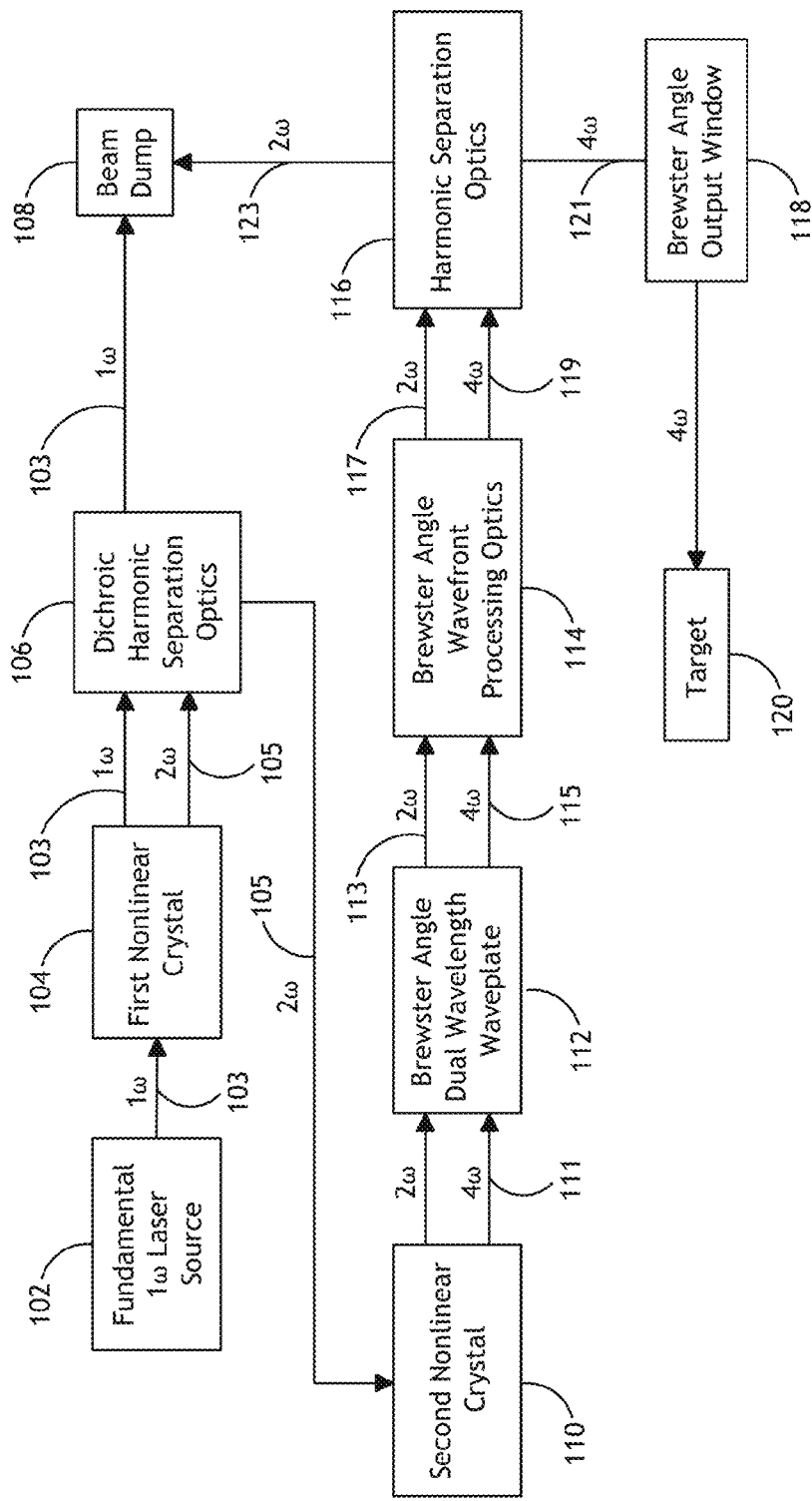
FIG. 1 illustrates a block diagram of an apparatus for laser frequency conversion with a high damage threshold, in accordance with an embodiment of the present invention.

FIG. 1 illustrates a block diagram view of a frequency conversion system 100 with high damage threshold, in accordance with one or more embodiments of the present disclosure. In one aspect, the system 100 may include a fundamental laser light source 102 configured to generate laser light 103 of a fundamental wavelength (e.g., wavelength of $\omega$), a first non-linear optical crystal 104 configured to receive the fundamental laser light 103 and frequency convert at least a portion of the fundamental light 103 to a first alternate wavelength light 105 (e.g., light having a wavelength of $2\omega$), and a second non-linear optical crystal 110 configured to receive the first alternate wavelength light 105 generated by the first optical crystal 104 and frequency convert at least a portion of the first alternate wavelength light 105 to second alternate wavelength light 111 (e.g., light having a wavelength of $4\omega$). In a further aspect, the system 100 may include a set of dichroic harmonic separation optics 106 configured to separate the fundamental light 103 and the first alternate light 105 emanating from the first nonlinear optical crystal 104. In another aspect, the system 100 may include a Brewster angle dual wavelength waveplate 112 configured to rotate the polarization of the first alternate wavelength light 105 relative to the second alternate wavelength light 111 such that, following rotation, the first alternate wavelength light 113 and the second alternate wavelength light 115 have substantially the same polarization. In an additional aspect, the system 100 may include a set of Brewster angle wavefront processing optics 114 configured to condition (e.g., focus, collimate, correct, or the like) the first wavelength light 113 and the second wavelength light 115 following processing by the dual wavelength waveplate 112. In another aspect, the system 100 may include a set of harmonic separation optics 116 configured to separate the first alternate wavelength light 117 (e.g., $2\omega$) from the second alternate wavelength light 119 (e.g., $4\omega$) following emanation from the wavefront processing optics 114. Applicant notes that throughout the present disclosure the term "harmonic separation optics" is used interchangeably with "harmonic separator." Further, the system 100 may include one or more Brewster angle output windows 118 configured to transmit the second alternate wavelength light 121 from the interior of the system 100 to a selected target 120.

In a general sense, the fundamental laser light source 102 may include any laser light source known in the art. The particular choice of wavelength of the fundamental laser light source 102 may depend on a variety of factors, including, but not limited to, the desired output wavelength of the alternate wavelength light generated by the non-linear response of the first non-linear optical crystal 104 or the second non-linear optical crystal 110.

Further, the first and second non-linear optical crystals 104, 110 of the system 100 may include any non-linear optical crystal known in the art. The particular choice of the non-linear optical crystal may depend on a variety of factors, including, but not limited to, the desired output wavelength of the alternate wavelength light generated by the non-linear response of the optical crystals 104, 110. In this sense, the choice of the fundamental laser light source 102 and the optical crystals 104 and 110 are typically made in conjunction, wherein a particular combination of the fundamental laser light source 102 and the first non-linear optical crystal 104 and the second non-linear optical crystal 110 are chosen such that the set produce the desired output alternate wavelength light 111. The particular choice of the fundamental light source 102, the optical crystals 104 and 110, the first generated alternate wavelength light 105, or the second generated alternate wavelength light 111 are not limiting, and it should be recognized by those skilled in the art that any choice of the above are within the scope of the present invention.

In one embodiment of the present invention, the dichroic separation optics 106 configured to separate the fundamental wavelength light 103 from the first alternate wavelength light 105 emanating from the first nonlinear optical crystal 104 may include, but are not limited to, a dichroic mirror. In this manner, the dichroic mirror may be arranged to transmit the fundamental light 103 to a beam dump 108, while directing the first alternate light 105 to the second nonlinear optical crystal 110. It should be recognized, however, that this description is not limiting and numerous other frequency separating technologies may be utilized within the scope of the present invention. While it is recognized herein that uncoated optics may be used to separate the fundamental wavelength light 103 from the first alternate wavelength light 105, it is anticipated that the first alternate wavelength light 105 (e.g., second harmonic light) is likely to be greater than 400 nm. At wavelengths of this size, optical coatings typically provide suitable damage thresholds.

While the configuration depicted in FIG. 1 is suitable for second harmonic generation, it is recognized herein that other types of frequency conversion or frequency mixing process may be implemented within the scope of the present invention.

The present invention is further directed to a system suitable for separating the divergent and copropagating first alternate wavelength beam 105 and the second alternate wavelength beam 111 after they emerge from the second nonlinear optical crystal 110 in order to isolate the selected frequency converted beam (e.g., beam having frequency of $4\omega$). In addition to isolating the high order beam, the system 100 may condition the illumination emanating from the second nonlinear optical crystal 110 by focusing, collimating, and/or correcting (e.g., correcting astigmatism) the beam of second alternate light 115 (e.g., beam having frequency of $4\omega$).

It recognized herein that, upon exiting the second nonlinear optical crystal 110, the second alternate light (e.g., 4ω) is often orthogonally polarized with respect to the first alternate light (e.g., 2ω). In a general sense, it is recognized herein that Brewster angle surfaces are highly efficient to P-polarized light, while being inefficient for S-polarized light. In this sense, a typical S-polarized reflection at the Brewster angle is only 16% of the original incident light. As such, the utilization of multiple Brewster angle reflections allows for the 100% efficient transmission of P-polarized second alternate wavelength light 111 (e.g., 4ω), with multiple stray reflections occurring for 5-polarized first alternate light 105 (e.g., 2ω). It is recognized that this behavior may lead to problems related to laser control, as the inconsistency is problematic with respect to laser control loops and feedback control. Applicant notes that the above description related to the polarization of the first alternate wavelength light 105 and the second alternate wavelength light 111 is not limiting and should merely be interpreted as an illustration. For example, it is anticipated that prior to processing by the waveplate 112, the second alternate wavelength light beam 111 may have polarization states other than pure P-polarization, while the first alternate wavelength light beam 105 may exhibit polarization states other than pure S-polarization.

In one aspect of the invention, the Brewster angle dual wavelength waveplate 112 of the system 100 may effectively rotate the polarization of the first alternate wavelength light 105 relative to the second alternate wavelength light 111 such that, following rotation of the polarization, the first alternate wavelength light 113 and the second alternate wavelength light 115 have substantially the same polarization. For example, in the case where the first nonlinear optical crystal 104 and the second nonlinear optical crystal 110 are both arranged in a second harmonic generation configuration, the Brewster angle dual wavelength waveplate 112 may effectively rotate the polarization of 2ω light transmitted through the second optical crystal 110 relative to the 4ω light generated by the second optical crystal 110, such that the 2ω and 4ω light emanating from the second optical crystal 110 have the same polarization. Further, the Brewster angle surfaces implemented throughout the present invention may be selected such that they are highly efficient to both wavelengths.

It is recognized herein that during processing by the Brewster angle dual wavelength waveplate 112 the polarization of the first alternate wavelength light 105 (2ω) is not rotated at the first surface of the dual wavelength waveplate 112. As such, there will be a single 16% reflection at the impinging surface of the dual wavelength waveplate for S-polarized first alternate wavelength light 105 (2ω). It is further recognized that the polarization of the first alternate wavelength light 105 (2ω) is rotated by the time it reaches the subsequent surfaces of the dual wavelength waveplate 112. As such, there is minimal loss observed at the subsequent surfaces of the dual wavelength waveplate 112. After processing by the dual wavelength waveplate 112, the exiting first alternate wavelength light 113 (2ω) has a polarization which is the same as the polarization of the exiting second alternate wavelength light 115 (4ω).

In another aspect of the invention, the Brewster angle wavefront processing optics 114 may condition the wavefront of the beam emerging from the dual wavelength waveplate 112, consisting of first alternate wavelength light 113 (2ω) and the second alternate wavelength light 115 (4ω). For example, the Brewster angle wavefront processing optics 114 may include a set of lenses oriented at the Brewster Angle and configured to collimate, correct (e.g., correct astigmatism), or focus the wavefront of the beam emerging from the waveplate 112. It is contemplated herein that the lenses of the set of Brewster angle wavefront processing optics 114 may be used on-axis or at small angles from the axis due to the large amount of astigmatism produced by tilting one or more lenses, as shown in greater detail further herein. It is recognized, however, that an off-axis cylindrical lens element may be implemented in order to correct for all or a portion of the astigmatism. As such, the implemented wavefront processing optics may both collimate and correct for the astigmatism typically produced in the frequency conversion process (e.g., frequency conversion process taking place in second non-linear optical crystal 110). It is further recognized that the Brewster's angle lens is likely only practical for small variations in the angle of incidence around Brewster's angle. Large variations in the angle of incidence may produce additional intensity roll off in the processed beam. It is further contemplated that additional Brewster's angle lenses may also be implemented.

In an additional aspect of the present invention, the harmonic separation optics 116 (i.e., the harmonic separator) may separate the first alternate wavelength light 117 (2ω) from the second alternate wavelength light 119 (4ω) emanating from the wavefront processing optics 114. The harmonic separation optics 116 may include a Brewster Angle input surface, a total internal reflection (TIR) surface, and a Brewster Angle output surface. As will be discussed in greater detail further herein, it is recognized that the harmonic separation optics 116 of the present invention may include various configurations. It is further contemplated herein that the TIR surface of the harmonic separation optics 116 may be engineered to produce TIR for the second alternate wavelength light 119 (4ω), while transmitting the first alternate wavelength light 117 (2ω).

In another aspect of the present invention, after harmonic separation, the second alternate wavelength light beam 121 (4ω) may be transmitted through a Brewster angle output window 118. For example, the second alternate wavelength light beam 121 (4ω) may be transmitted through one or more Brewster angle output windows 118 toward a selected target 120. In addition, the first alternate wavelength light beam 123 (2ω) may be utilized in another capacity (e.g., directed at a target required first alternate wavelength light) or transmitted to a beam dump 108.

The applicant notes that since the entire optical path for the second alternate wavelength light (4ω) utilizes Brewster angle surfaces and TIR surfaces, approximately 100% transmission of the second alternate wavelength light (4ω) is attainable.

While the above description focuses on the implementation of the system 100 with a first crystal 104 and a second crystal 110 and each of the processing elements including the Brewster angle dual wavelength waveplate 112, the Brewster angle wavefront processing optics 114, and the harmonic separation optics 116, it is further contemplated herein that the system 100 does not require each of these components. For example, it is contemplated herein that the system 100 may include a single nonlinear optical crystal, with the output of the single nonlinear optical crystal being fed into the various Brewster angle processing components described previously herein. Further, it is contemplated herein that the system 100 may include one or more of the processing components including the Brewster angle dual wavelength waveplate 112, the Brewster angle wavefront processing optics 114, and the harmonic separation optics 116. As such, the description throughout the present disclosure relating to specific configurations of the frequency conversion system of the present invention should not be interpreted as limiting, but merely illustrative.

Figure 2:
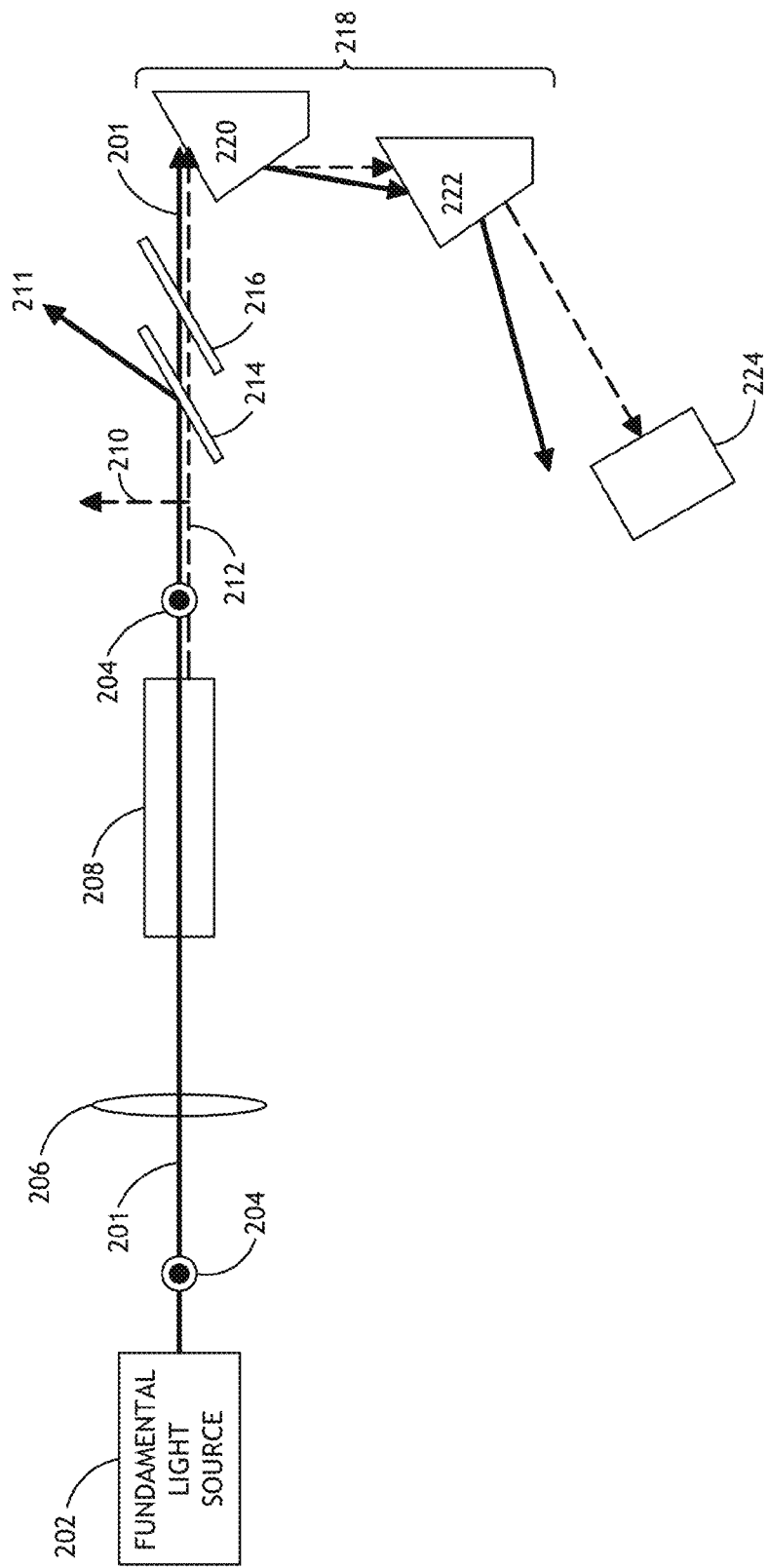
FIG. 2 illustrates a schematic diagram of an apparatus for laser frequency conversion with a high damage threshold, in accordance with an embodiment of the present invention.

FIG. 2 illustrates a schematic view of a single nonlinear optical crystal 208 based frequency conversion system 200, in accordance with one or more embodiments of the present invention. In one aspect, the system 200 includes a fundamental light source 202, a focusing element 206, a single nonlinear optical crystal 208, a Brewster angle dual wavelength waveplate 214, Brewster angle wavefront processing optics 216, and harmonic separation optics 218.

For the purposes of the present disclosure it is assumed that the single nonlinear crystal 208 is configured to receive horizontally polarized 204 fundamental laser light 201 having a frequency of 532 nm from the fundamental laser light source 202. Further, the optical crystal 208 is configured to frequency convert at least a portion of the received horizontally polarized 532 nm light to vertically polarized 210 alternate wavelength light 212 having a 266 nm wavelength. Applicant notes that the above description related to the frequency and polarization of the fundamental light 201 or the alternate wavelength light 212 is not limiting and should be interpreted merely as an illustration. Further, it is also contemplated herein that the system 200 may incorporate the concepts discussed with respect to system 100. Likewise, it is further contemplated that the following description of system 200 and the various components thereof should be interpreted to extend to system 100. For instance, although not shown, rather than a single nonlinear optical crystal the system 200 may include a first nonlinear optical crystal configured to generate first alternate wavelength light and a second nonlinear optical crystal configured to generate second alternate wavelength light. As such, the description related to system 100 should be interpreted to extend to system 200.

In one aspect, the focusing element 206 is disposed along an optical pathway between the fundamental light source 202 and the nonlinear optical crystal 208. In this regard, the focusing element 206 is configured to focus the fundamental light 201 emanating from the fundamental light source 202 into the nonlinear optical crystal 208.

It is noted herein that the arrangement described above relating to the position of the focusing element 206 is not limiting and should merely be interpreted as illustrative in nature. In a further embodiment, the focusing element 206 may include any optical devices known in the art suitable for focusing the fundamental laser light 201 emanating from the fundamental laser light source 202. For example, the first focusing element 206 may include, but is not limited to, a lens, a mirror, or a diffractive element.

It is contemplated herein that focusing of the fundamental laser light 201 is not a requirement of the system 200. In this sense, whether focusing of the fundamental laser light 201 is required may depend, for example, on the required beam size within the optical crystal 208.

The focusing element 206 may focus horizontally polarized 532 nm light through the nonlinear crystal 208 in order to generate 266 nm vertically polarized light. After frequency conversion inside the nonlinear optical crystal 208 the alternate wavelength light 212 (266 nm) having a vertical polarization 210 copropagates with residual fundamental light 201 (532 nm) having a horizontal polarization 204 toward the Brewster angle dual wavelength waveplate 214.

In another aspect of the present invention, upon emanating from the nonlinear optical crystal 208, the alternate wavelength light 212 (266 nm) and the residual fundamental light 201 (532 nm) is processed by the Brewster angle dual wavelength waveplate 214. In a general sense, those skilled in the art should recognize that a dual wavelength waveplate is capable of providing a specific retardance at two different wavelengths. The dual wavelength waveplate 214 of the present invention may include any known dual wavelength waveplate known in the art. For example, the dual wavelength waveplate 214 may include, but is not limited to, a crystal quartz based dual wavelength waveplate.

In one embodiment, the Brewster angle dual wavelength waveplate 214 may include a first surface at S-polarization for the fundamental light (532 nm) and at P-polarization for the alternate wavelength light (266 nm). As such, the surface reflects approximately 16% of the fundamental light 201 impinging on the first waveplate surface, while transmitting approximately 100% of the alternate wavelength light 212. In a further embodiment, the dual wavelength waveplate 214 may be constructed to provide full wave retardation at the alternate light wavelength (266 nm), while providing half wave retardation at the fundamental light wavelength (532). As such, the waveplate 214 does not rotate the polarization of the alternate light 212, while the waveplate 214 does rotate the polarization of the fundamental light 204, so that the fundamental light (532 nm) is also at Brewster's angle and there is minimal reflection at the second surface of the waveplate 214.

Figure 3A:
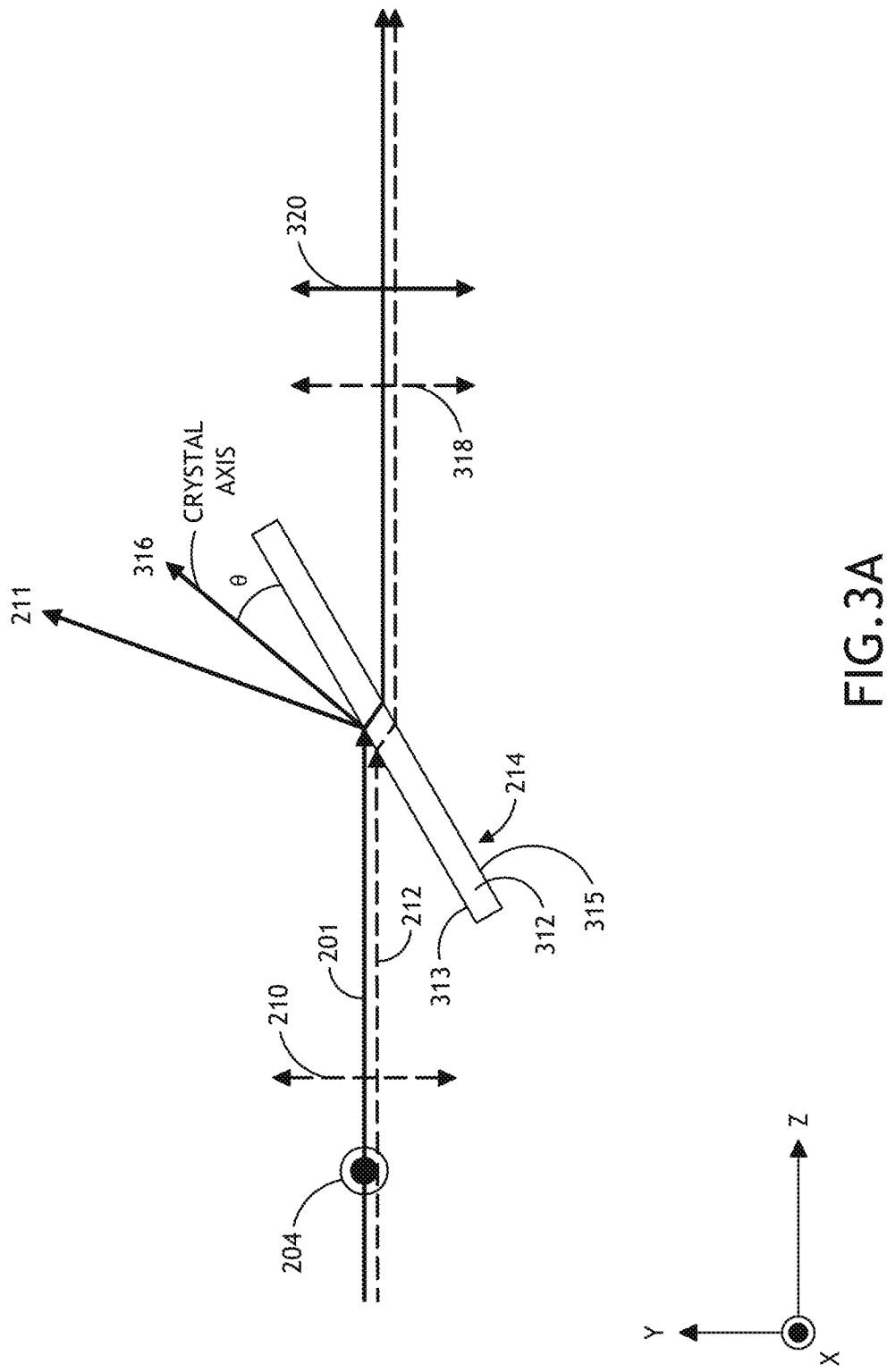
FIGS. 3A-3B illustrate a schematic diagram of a Brewster angle dual wavelength waveplate of the apparatus for laser frequency conversion with a high damage threshold, in accordance with an embodiment of the present invention.
Figure 3B:
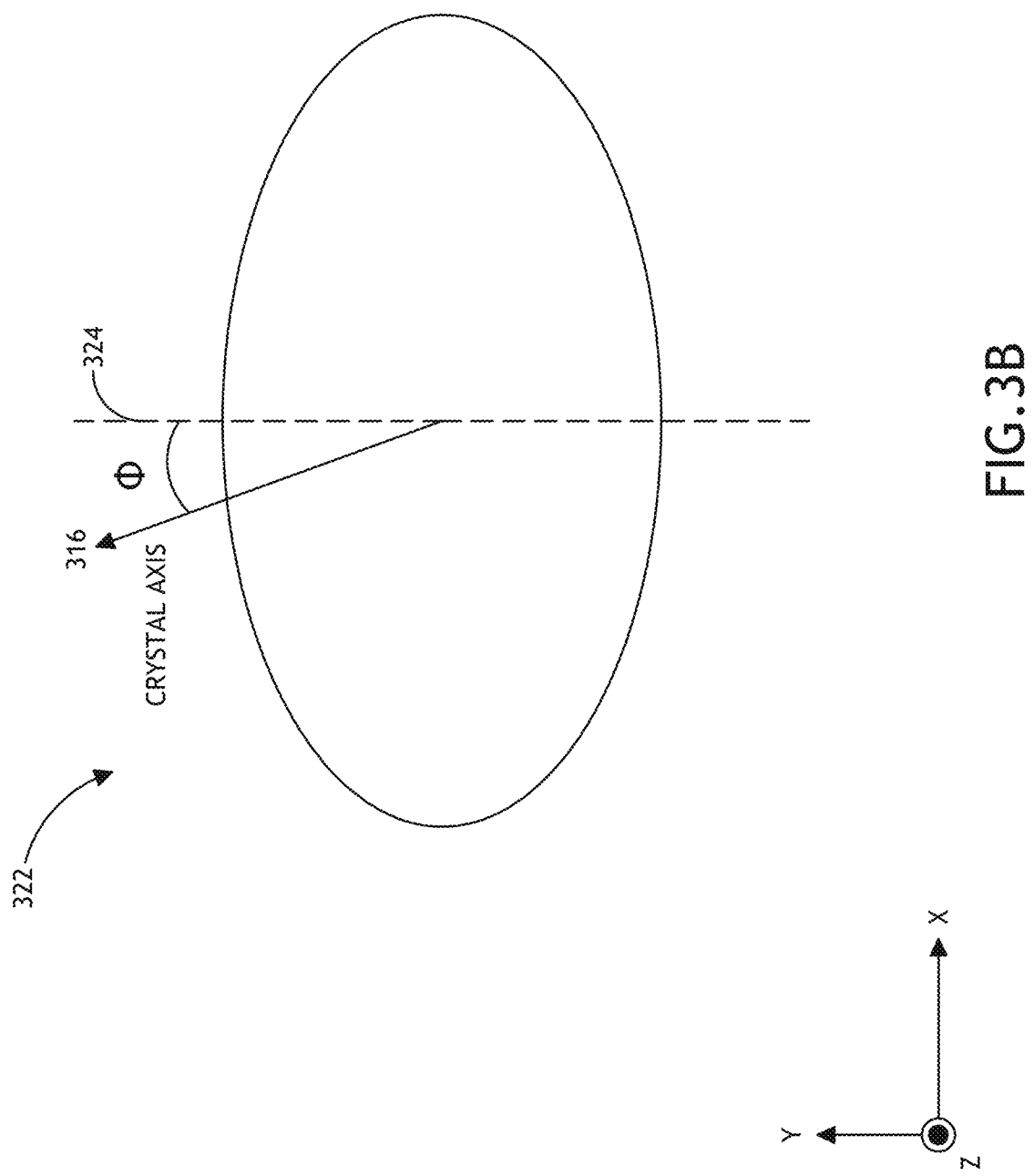

FIGS. 3A and 3B illustrate a schematic view of a Brewster angle dual wavelength waveplate 214, in accordance with one embodiment of the present invention. The dual wavelength waveplate 214 of FIG. 3A may include, but is not limited to, a single birefringent plate 312. Those skilled in the art should recognize that commercially available waveplates typically are used at normal incidence, with the optical axis of the crystal within the surface of the waveplate. In this sense, commercial waveplates are typically used to rotate polarizations to various angles by rotating polarization about the axis normal to the waveplate surface. It is further recognized that multiple order dual wavelength waveplates may be implemented. However, because of the associated material dispersion, the performance at one of the wavelengths is typically not optimum. Further, the utilization of waveplates at normal incidence is common because the normal incidence geometry simplifies the manufacturing process as the optical axis resides within the surface of the plate, dramatically simplifying the effort required to solve the required crystal orientation.

In the case of Brewster angle incidence, there exist three primary classes of solutions to the required orientation. The three classes of solutions include: 1) a single plate with the crystal axis out of the plate surface; 2) a single plate with the crystal axis in the plate surface; and 3) dual plates with the crystal axis within the plate surface.

As shown in FIG. 3A, the waveplate 214 of FIG. 3A consists of a single plate 312 having a crystal axis out of the plate surface. Input S-polarized fundamental light 304 (e.g., wavelength of 532 nm) and P-polarized alternate light 306 (e.g., wavelength of 266 nm) may impinge on a surface of the waveplate 214 at Brewster's angle. For example, in the case of 266 nm light and a crystal quartz waveplate, the Brewster angle is 58 degrees. It is noted herein that the implemented angle of incidence is approximately equal to Brewster's angle, which depends on the index of refraction of the receiving waveplate, which in turn is dependent on the wavelength of the incident light beam. As such, the implemented angle of incidence for the dual wavelength waveplate is a function of the material utilized in the plate as well as the wavelength of the light impinging on the waveplate.

It is noted that a portion of the impinging fundamental light 304 (532 nm) light will reflect 314 off a first surface 313 of the single plate 312. It is further noted that the crystal axis 316 is rotated at an angle θ with respect to the waveplate surface 313 and at an angle φ with respect to the polarization axis 324 of the alternate wavelength light (266 nm), as shown by 322 of FIG. 3B.

In one embodiment, the thickness of the plate 312 and the angle of the crystal axis may be chosen such that the alternate wavelength light 306 (266 nm) is retarded by exactly one full wave and the fundamental light 204 (532 nm) is within 99% of half wave retardation. In this orientation, the alternate wavelength light (266 nm) experiences no change in propagation through the single waveplate 312, while the fundamental wavelength light 204 (532 nm) experiences a polarization rotation of 90 degrees. It is recognized herein that because the single waveplate 312 is oriented at Brewster's angle for the alternate wavelength light 212 (266 nm), there is no theoretical loss at this wavelength. The fundamental wavelength light 204 (532 nm), however, as it has S-polarization for the first surface of the waveplate 312, experiences approximately 16% reflection at the first surface 313.

In another embodiment, the plate 312 may be configured to provide full wave retardation at the fundamental wavelength and half wave retardation at the alternate wavelength. In an alternative embodiment, the plate 312 may be configured to provide half wave retardation at both the fundamental wavelength and the alternate wavelength.

It is further noted that once the alternate wavelength light 212 (532 nm) reaches the second surface 315 of the single plate 312, the polarization is rotated to P-polarization. The reflectivity of fundamental light 204 (532 nm) P-polarized light at an interface that is at Brewster's angle for the alternate wavelength light 212 (266 nm) is only approximately 0.05%, resulting in very little loss. As such, the single birefringent plate 312 of FIG. 3 is suitable for effectively rotating the fundamental laser light 204 (532 nm) polarization to the same polarization of the alternate wavelength light 212 (266 nm) with only a single, but manageable, reflection of the fundamental light 201.

It is noted that while the above description focuses on fundamental light and alternate light having 532 nm and 266 nm wavelengths respectively, it is recognized herein that the concepts above may be extended to other incident wavelengths and orientation angles.

Figure 4A:
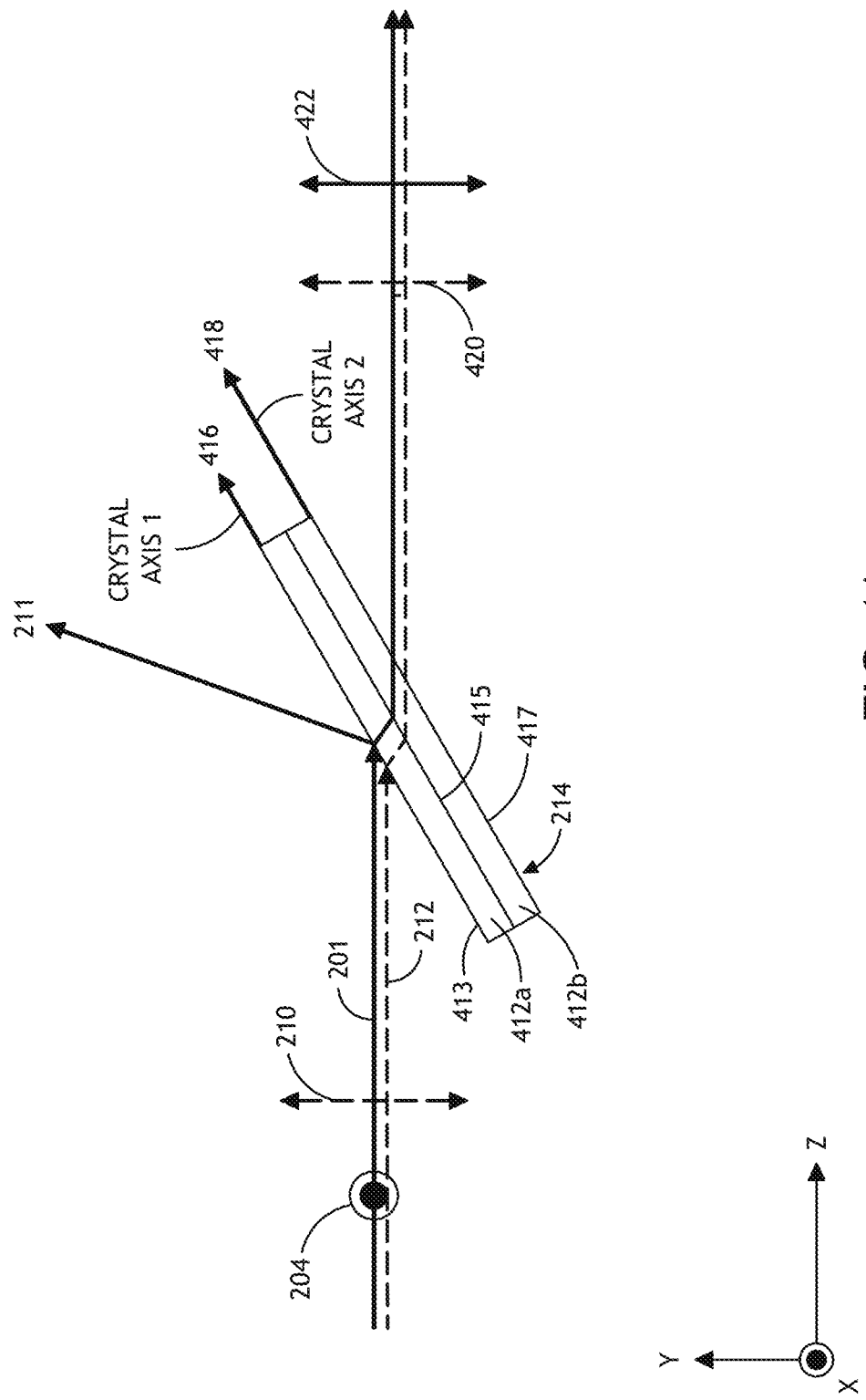
FIGS. 4A-4B illustrate a schematic diagram of a Brewster angle dual wavelength waveplate of the apparatus for laser frequency conversion with a high damage threshold, in accordance with an embodiment of the present invention.
Figure 4B:
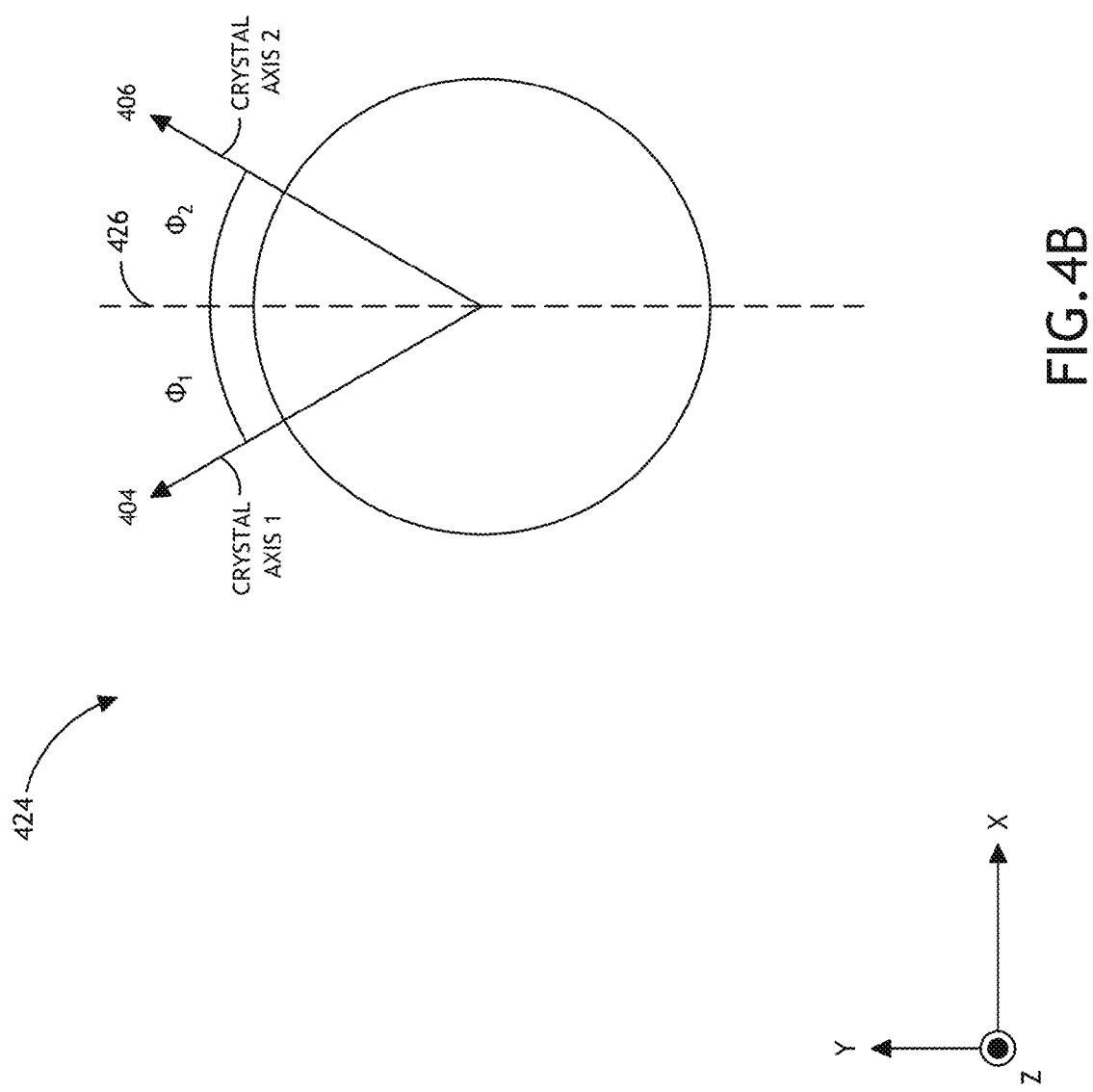

FIGS. 4A and 4B illustrate a schematic view of a Brewster angle dual wavelength waveplate 214, in accordance with one embodiment of the present invention. The dual wavelength waveplate 214 of FIG. 4A includes a differential waveplate 214 consisting of a first plate 412a and a second plate 412b optically coupled to the first plate 412a. Further, the second plate 412b may act to correct at least a portion of the phase variations introduced by the first plate 412a.

Those skilled in the art should recognize the difficulty that exists in trying to manufacture a free standing waveplate that is less than 300 μm in thickness. Waveplates that are thicker than this size often display increased sensitivity angle, which is problematic when the given waveplate must be utilized over a range of angles. The waveplate 214 design of FIG. 4A is less sensitive to variations in the angle of incidence and further allows for increased plate thickness, which further simplifies the manufacturing process.

The first plate 412a and the second plate 412b of the dual wavelength waveplate 214 may be coupled together in manner known in the art. In one embodiment, the first plate 412a and second plate 412b may be optically coupled such that an air gap exists at the interface 415 between the two plates. In another embodiment, the first plate 412a and second plate 412b may be coupled together utilizing an epoxy. In yet another embodiment, the first plate 412a and second plate 412b may optically contacted or bonded together.

FIG. 4A illustrates a dual wavelength Brewster angle waveplate 214 having a first plate 412a and the second plate 412b optically bonded together. In one aspect, the crystal axis 416 of the first plate 412a and the crystal axis 418 of the second plate 412b are in the planes of the respective plates, as shown in FIG. 4A. As previously discussed, impinging alternate wavelength light 2212 (266 nm) is P-polarized, while impinging fundamental wavelength light 201 (532 nm) is S-polarized.

In another aspect, the waveplates 412a and 412b are set at Brewster's angle for 266 nm light. At the first surface 413 of the dual wavelength waveplate 214, approximately 16% of the fundamental light 201 (532 nm) is reflected 211, while the alternate wavelength light 212 (266 nm) experiences zero or nearly-zero reflection at the first surface 413 and is allowed to efficiently pass through the waveplate 214.

In one embodiment, the thickness of the first waveplate 412a may be selected such that it behaves as a full waveplate at the alternate wavelength (266 nm) and a half waveplate at the fundamental wavelength (532 nm). This configuration minimizes any reflection at the interface 415 between first waveplate 412a and the second waveplate 412b of the dual wavelength waveplate 214. In another embodiment, the thickness of the second waveplate 412b may be chosen such that the difference in thickness is equivalent to the thinnest available single waveplate solution for the dual wavelength Brewster angle waveplate 214.

In an additional embodiment, the crystal axis 416 of the first waveplate 412a is orientated at an angle φ1 with respect to the polarization axis 426 of the alternate wavelength light 212 (266 nm), while the crystal axis 418 of the second waveplate 412b is oriented at an angle φ2 with respect to the polarization axis 426 of the alternate wavelength light 212 (266 nm). It is recognized herein that when φ1 is equal and opposite to φ2 the second waveplate 412b acts to cancel out at least a portion of the retardance of the first waveplate 412a, resulting in a differential dual wavelength Brewster angle waveplate. It is further recognized herein that the differential solution is less sensitive to changes in angle of incidence, temperature, alignment, and the like.

The birefringent plates of the dual wavelength waveplate 214 may be fabricated from any suitable material known in the art. For example, material used to fabricated the one or more birefringent plates of the dual wavelength waveplate 214 may include crystal quartz, magnesium fluoride, sapphire lithium niobate, or a rutile based compound.

Referring again to FIG. 2, upon emanating from the Brewster angle dual wavelength waveplate 214, the vertically polarized alternate wavelength light 212 (266 nm) and the vertically polarized residual fundamental light 201 (532 nm) are further conditioned utilizing a set of Brewster angle wavefront processing optics 216. The wavefront processing optics 216 of the present invention may include focusing optics, collimating optics, or correction optics. In one embodiment, the lens or set of lens of the wavefront processing optics 216 may be configured to collimate, focus, and/or correct the alternate light 212 (266 nm) after it emanates from the dual wavelength waveplate 214. It is recognized herein that this configuration may produce residual aberrations that may be corrected once the beams are separated. Applicant notes herein that the optical elements of the Brewster angle wavefront processing optics 216 may include any optical devices known in the art capable of carrying out the correction, collimation, or focusing as required by the system 200.

Figure 5:
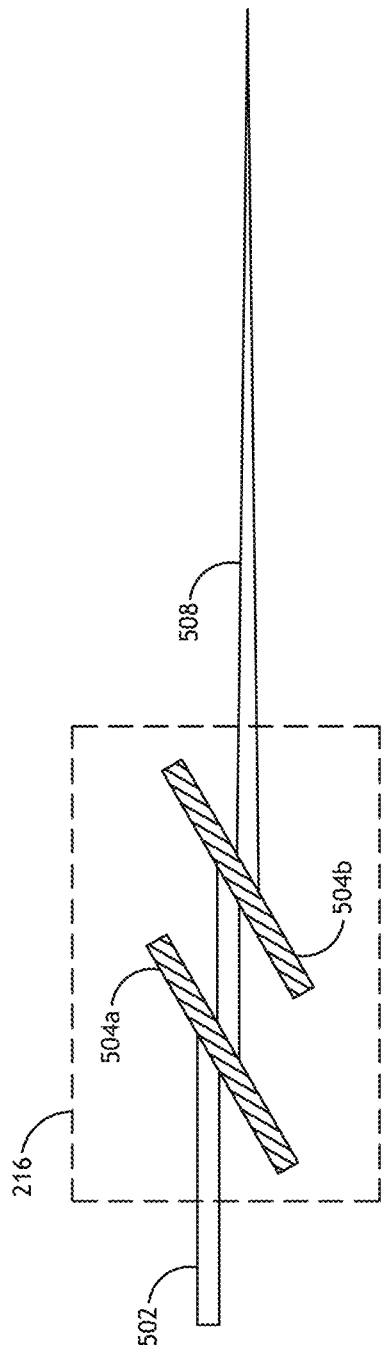
FIG. 5 illustrates a schematic diagram of a set of Brewster angle wavefront processing optics of the apparatus for laser frequency conversion with a high damage threshold, in accordance with an embodiment of the present invention.

FIG. 5 illustrates a schematic view of a set of Brewster angle wavefront processing optics 216, in accordance with an embodiment of the present invention. As shown in the embodiment of FIG. 5, the Brewster angle wavefront processing optics 216 may include, but are not limited to, a first lens 504a and a second lens 504b. It is recognized herein that the lens or set of lenses (e.g., lenses 504a and 504b) of the processing optics 216 may be utilized at normal incidence or at small angles in order to minimize aberrations within the system. It is further recognized that titling of one or more of lenses used to process light may cause astigmatism in the processed light. In addition, decentering of one or more of the lenses may produce coma in the processed light. The Brewster angle wavefront processing optics 216, among other things, are configured to minimize the effects of aberration, astigmatism, and coma utilizing one or more surfaces oriented at the Brewster angle.

It is recognized herein that in order for light 502 (e.g., fundamental light and/or alternate light) to experience low reflections over the entire beam the angles of incidence should extend over a small range about the Brewster angle. In order to meet this requirement processing optics 216 may include lenses having a long radius of curvature, while the incident light may include light having a high F number (e.g., F number of 50 or higher). It is anticipated that the use of a F number equal to or above 50 along with a lens design having a suitably long radius of curvature may maintain the required low angle of incidence.

In one embodiment, as illustrated in FIG. 5, the wavefront processing optics 216 may include a fully corrected two lens system with all surfaces being at the Brewster's angle. In one embodiment, the first lens 504a of the wavefront processing optics 216 may have a first surface that has a spherical curvature and a second surface that is planar. Further, the second lens 504b of the processing optics 216 may have a first surface that is planar and second surface that has cylindrical curvature. The cylindrical curvature of the second lens 504b acts to correct for the astigmatism of the tilted spherical surface of the first lens 504a and aids in producing an output beam 508 with no net astigmatism. It is further noted that the output beam 508 is displaced relative to the input beam 502 as it propagates through both lenses 504a and 504b. In a further embodiment, the lens system may be engineered such that the center of the input beam 502 passes through the point on the curved surface of the first lens 504a where the angle between the surface normal of the lens 504a and the beam propagation axis are at Brewster's angle.

In another embodiment, the first and second lenses 504a and 504b of the wavefront processing optics 216 may be configured to produce a selected focal length. For example, the lens design of the wavefront processing optics 216 of FIG. 5 may include a lens design with a focal length of 155 mm.

It is further recognized herein that the lens design of the wavefront processing optics 216 may be selected to produce varying degrees of residual astigmatism. This ability may then be used to correct for astigmatism that typically exists in frequency converted lasers.

Figure 6:
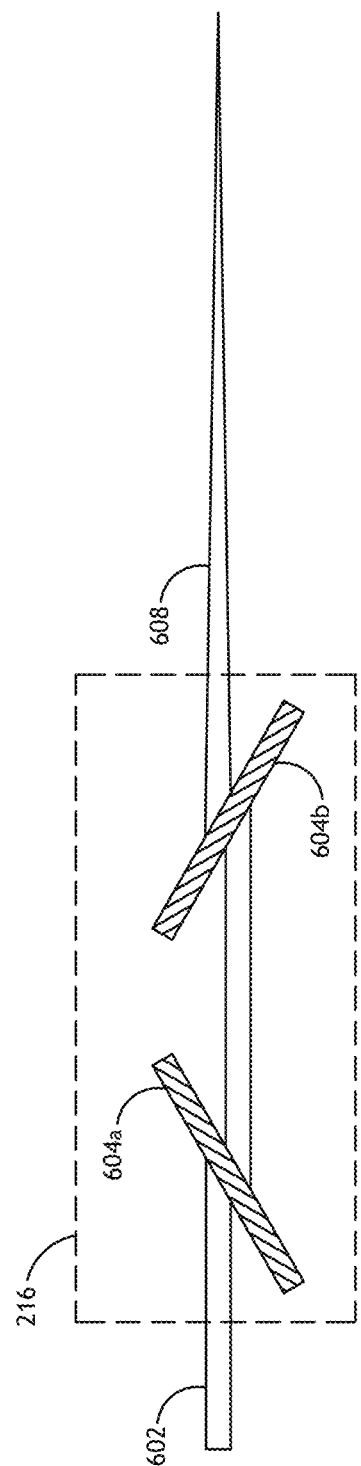
FIG. 6 illustrates a schematic diagram of a set of Brewster angle wavefront processing optics of the apparatus for laser frequency conversion with a high damage threshold, in accordance with an embodiment of the present invention.

FIG. 6 illustrates a schematic view of a set of Brewster angle wavefront processing optics 216, in accordance with an alternative embodiment of the present invention. In this embodiment, the first lens 604a may be oriented at Brewster's angle, with the second lens 604b may be oriented at the Brewster angle, but in a compensating direction, as shown in FIG. 6. In this sense, the cylindrical surface of the second lens 604b is oriented at an angle of 90 degrees relative to the cylindrical surface of the second lens 504b of the embodiment illustrated in FIG. 5. It is recognized herein that if both lenses 604a and 604b are made with the same center thickness, the output beam 608 should experience no net displacement relative to the input beam 602. It is further recognized herein that the configuration illustrated in FIG. 6 may be implemented in a frequency conversion system in order to simplify system alignment.

In another embodiment, the wavefront processing optics 216 may include a lens system configured to correct for astigmatism by adding astigmatism with no net focusing power. For example, an input wavefront having a measured level of astigmatism may be corrected using two elements each having a cylindrical surface such that output wavefront has zero residual astigmatism. For instance, an input wavefront with 3.3278 waves of astigmatism may be corrected using two elements each having a cylindrical surface such that the residual astigmatism of the output beam is zero to within numerical error.

In another embodiment, the amount of astigmatism present in a given beam may be dynamically adjusted by changing the axial separation of the first lens (e.g., 504a or 604a) and the second lens (e.g., 504b or 604b). It is recognized herein that the dynamic adjustment of astigmatism allows for fine tuning the astigmatism correction during initial alignment and correcting for changing astigmatism as the frequency converted laser ages. It is further contemplated that this dynamic astigmatism correct may be carried out utilizing an astigmatism measurement system, a computer system, and one or more translation stages communicatively coupled in a feedback loop.

Referring again to FIG. 2, upon emanating from the Brewster angle wavefront processing optics 216, the alternate wavelength light 212 (266 nm) and the residual fundamental light 201 (532 nm) may be transmitted through one or more Harmonic Separation Optical elements 218. Applicant again notes that throughout the present disclosure the term "harmonic separation optical elements" is used interchangeably with "harmonic separator." The harmonic separation optics 218 may include one or more Brewster Angle-TIR harmonic separation elements. It is recognized herein that a variety of harmonic separation configurations may be implemented within the present invention, as will be described in greater detail further herein. For example, it is recognized that the one or more harmonic separation optical elements 218 may include a single harmonic separation element or multiple harmonic separation elements.

For instance, the harmonic separator 218 may include a first harmonic separation element 220 and a second harmonic separation element 222. It is recognized herein that the second harmonic separation element 222 may be implemented in order to further increase the angular separation of the harmonics (i.e., the fundamental light beam and the alternate wavelength light beam) allowed for the reduction in size of the given frequency conversion system. In another instance, a second harmonic separation element may be implemented in order to redirect the beam independent of the harmonic separation.

Figure 7:
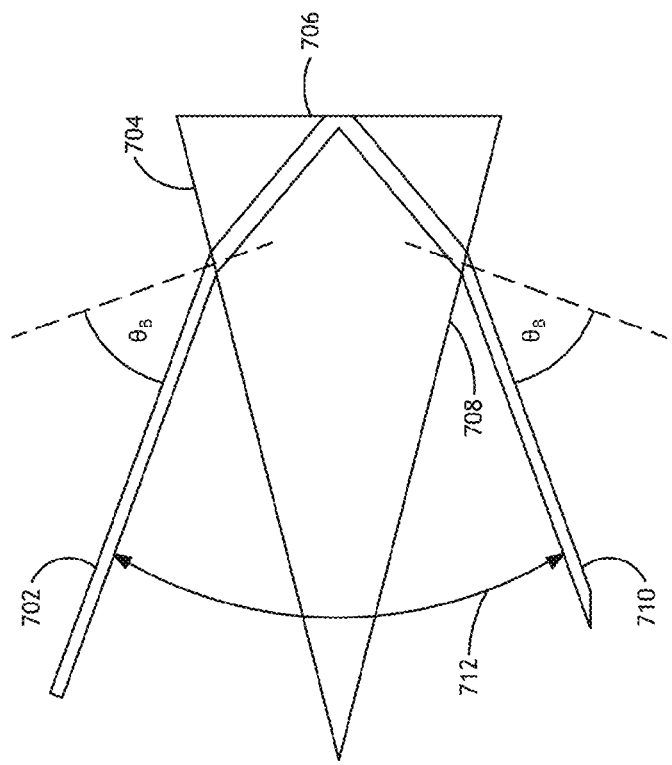
FIG. 7 illustrates a schematic diagram of a harmonic separator of the apparatus for laser frequency conversion with a high damage threshold, in accordance with an embodiment of the present invention.

FIG. 7 illustrates a Brewster angle-Total internal Reflection (TIR) reflector element 700 suitable for implementation as a harmonic separation optical element of the harmonic separator 218 of the present invention. It is recognized herein that ideally the light impinging on the harmonic separation element 700 is highly P-polarized, improving the efficiency of the element 700. It is noted, however, that this is not a requirement of the invention.

In one embodiment, a first optical surface 704 of the element 700 receives light at Brewster's angle $\theta_B$. The light is then transmitted through a portion of the element 700 and undergoes TIR on a second surface 706 of the element 700. The light then exits through a third surface 708 of the element 700 oriented at Brewsters angle $\theta_B$.

It is recognized herein that if two wavelengths (e.g., 532 nm for fundamental wavelength light and 266 nm for alternate wavelength light) enter the harmonic separation element 700, the light of each wavelength will undergo different angles of refraction causing the beams to deviate from one another through the volume of the element 700. In this example, the second Brewster's angle surface may add an opposite angle to the angular deviation resulting in zero net angular change once the beams exit the element 700. It is noted that there may exist a residual spatial offset between the two beams, which is dependent on the length of propagation in within the element 700. In a further embodiment, this spatial offset may be corrected for utilizing a second Brewster Angle-TIR element if desired.

In another embodiment, the angle 712 between the incident light 702 and the exiting light 710 may be controlled by using different apex angles. The minimum deviation may be set by the requirement for TIR at the second surface 706.

It is recognized herein that the material of the harmonic separation element 700 may include any suitable material known in the art. For example, the material of the harmonic separation element 700 may include, but is not limited to, any glass or crystalline material. It is further recognized that in the UV-DUV range fused silica and calcium fluoride are particular advantageous.

Those skilled in the art should recognize that light beams of shorter wavelength light bend more significantly when entering a material with a higher index of refraction than the surrounding medium (e.g., air). As such, the harmonic separation element 700 may be configured such that the shorter wavelength light undergoes TIR, while longer wavelength is largely transmitted through the element 700. In this regard, the element 700 acts to separate the incident wavelengths of light.

In another embodiment, in the event only a single wavelength is incident on the element 700, the element 700 may be utilized as a zero loss, high damage threshold mirror.

Figure 8:
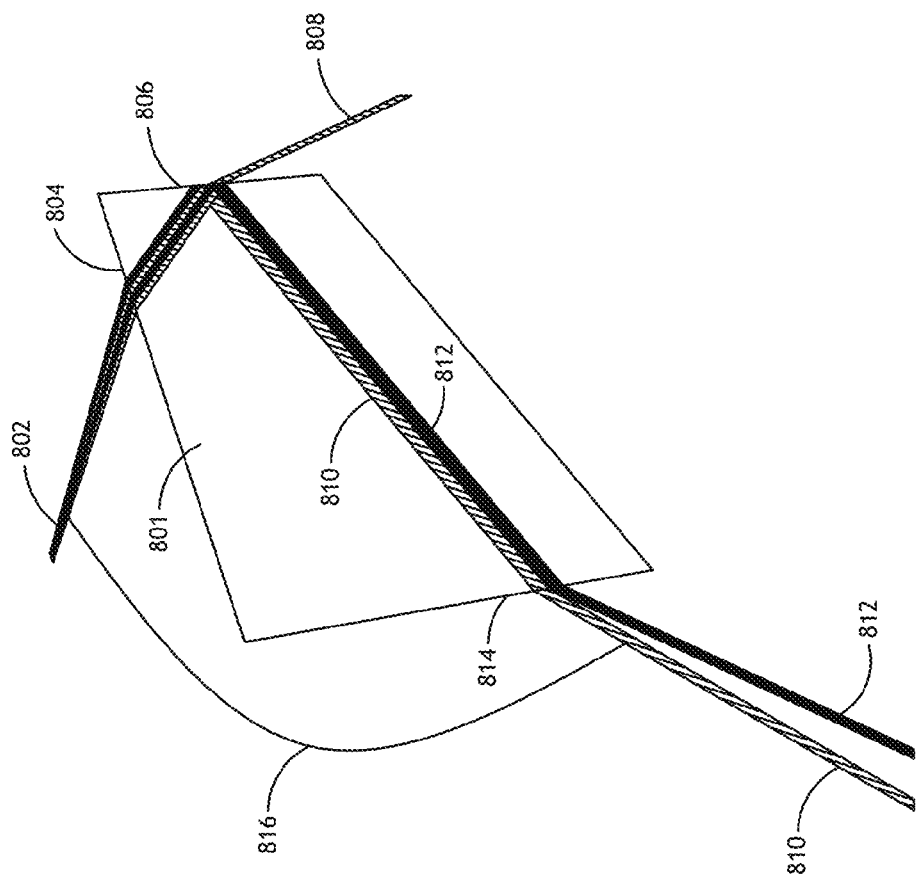
FIG. 8 illustrates a schematic diagram of a harmonic separator of the apparatus for laser frequency conversion with a high damage threshold, in accordance with an embodiment of the present invention.

FIG. 8 illustrates an alternative Brewster angle-Total internal Reflection (TIR) reflector element 800 suitable for implementation as a harmonic separation optical element 218 of the present invention. Applicant notes that for the purposes of the present disclosure the description related to FIG. 7 should be interpreted to extend throughout the remainder of the disclosure unless otherwise noted.

In one embodiment, a first optical surface 804 is configured to receive light at Brewster's angle $\theta_B$. The light is then transmitted through a portion of the element 800 and undergoes TIR on a second surface 806 of the element 800. At least a portion of the light then exits through a third surface 814 of the element 800 oriented at Brewster's angle $\theta_B$. It is noted herein that the second Brewster's angle surface 814 of the Brewster angle-TIR reflector element 800 is oriented in the negative or opposite direction as the second Brewster's angle surface 708 of the element 700 of FIG. 7.

It is again noted herein that if two or more wavelengths (e.g., 532 nm for fundamental wavelength light and 266 nm for alternate wavelength light) enter the harmonic separation element 800, the light of each wavelength will undergo different angles of refraction at the first Brewster surface 804 causing the beams 810, 812 to begin deviating from one another. In this example, the second Brewster's angle surface 814 may add an additional dispersion angle to the angular deviation. As the two wavelengths propagate after exiting the second Brewster angle surface 814 of the element 800 they will continue to increase their separation, until they are completely separated, allowing for the isolation of the two or more wavelengths of light.

In another embodiment, the angle 816 between the incident light 802 and the exiting light 810, 812 may be controlled by using different apex angles. The minimum deviation may be set by the requirement for TIR at the second surface 806.

It is again recognized that the material of the harmonic separation element 800 may include any suitable material known in the art. For example, the material of the harmonic separation element 800 may include, but is not limited to, any glass or crystalline material. It is further recognized that in the UV-DUV range fused silica and calcium fluoride are particular advantageous.

Due to shorter wavelength light bending more significantly when entering a material with a higher index of refraction, the harmonic separation element 800 may be configured such that the shorter wavelength light undergoes TIR at surface 806, while longer wavelength light (e.g., light 808) is largely transmitted through the through the element 800 and out of the surface 806. In this regard, the element 800 also acts to separate the incident wavelengths of light.

Figure 9:
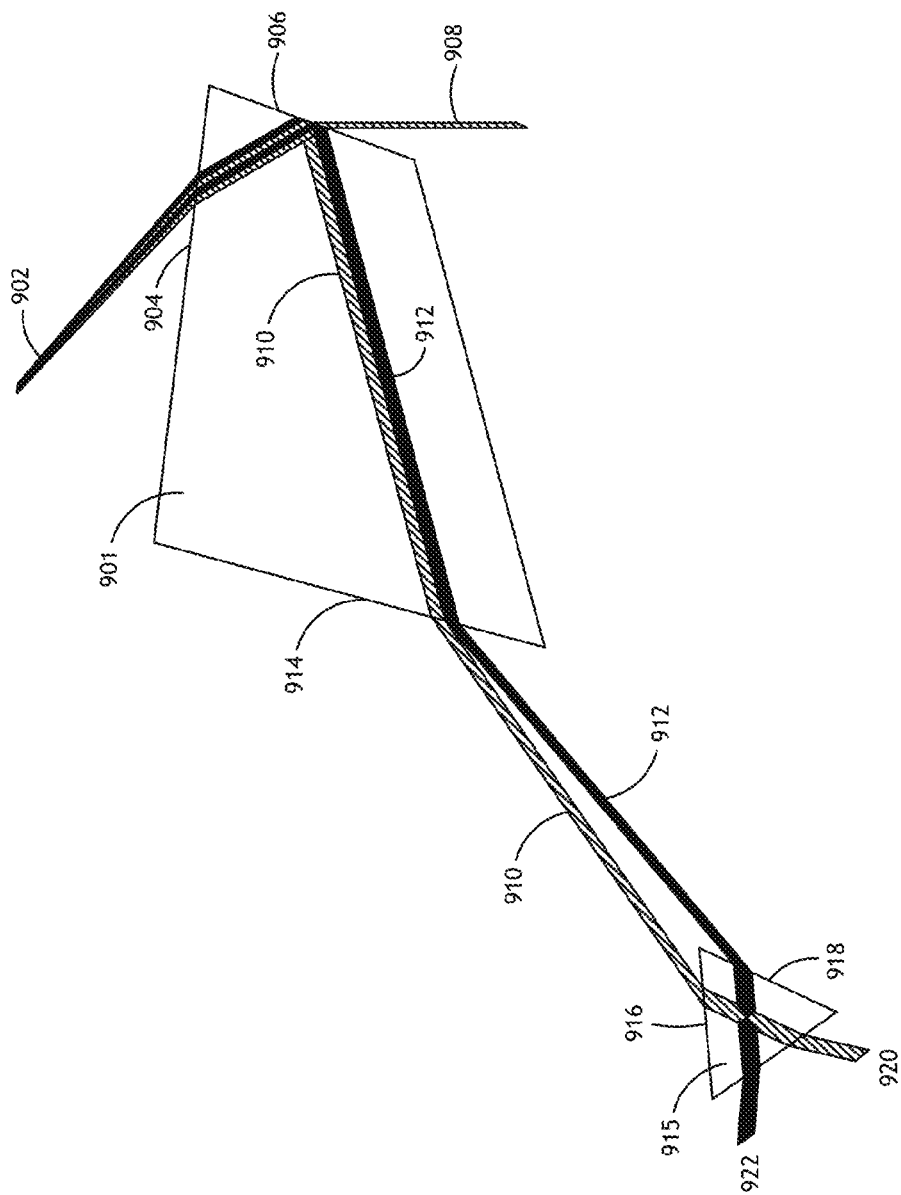
FIG. 9 illustrates a schematic diagram of a harmonic separator of the apparatus for laser frequency conversion with a high damage threshold, in accordance with an embodiment of the present invention.

FIG. 9 illustrates a combination 900 of a harmonic separation element 901 and a Brewster angle element 915, wherein the Brewster angle element 915 is implemented to increase the net angular deviation between light beams of two wavelengths emerging from the harmonic separation element 901. As noted previously, it is recognized herein that ideally the light impinging on the first harmonic separation element 901 is highly P-polarized, improving the efficiency of the elements 901 and 915. It is noted, however, that this is not a requirement of the invention.

In one embodiment, a first optical surface 904 is configured to receive light at Brewster's angle $\theta_B$. The light is then transmitted through a portion of the element 901 and undergoes TIR on a second surface 906 of the element 901. At least a portion of the light then exits through a third surface 914 of the element 901 oriented at Brewster's angle $\theta_B$.

It is again noted that if two or more wavelengths (e.g., 532 nm for fundamental wavelength light and 266 nm for alternate wavelength light) enter the harmonic separation element 901, the light of each wavelength will undergo different angles of refraction at the first Brewster surface 904 causing the beams 910, 912 to begin deviating from one another. In this example, the second Brewster's angle surface 914 may add an additional dispersion angle to the angular deviation. As the two wavelengths propagate after exiting the second Brewster angle surface 914 of the element 901 they will continue to increase their separation, until they impinge on the Brewster angle element 915.

In one embodiment, the input optical surfaces 916 and 918 of the Brewster angle element 915 may be oriented at Brewster's angle for the different impinging wavelengths (e.g., 532 nm for fundamental wavelength light and 266 nm for alternate wavelength light). It is recognized herein that since these Brewster surfaces 916, 918 have different signs, the difference in the refraction angles increases greatly. In a further embodiment, the output surface may be optimized at Brewster's angle for one of the wavelengths, typically the wavelength of interest (i.e., the alternate wavelength light). For example, an antireflection coating may be added to one section of the element 915 to further reduce the reflectivity.

The Brewster angle element 915 may be fabricated from any suitable material known in the art. For example, the material of the Brewster angle element 915 may include, but is not limited to, any glass or crystalline material, such as, but not limited to, fused silica and calcium fluoride.

Figure 10:
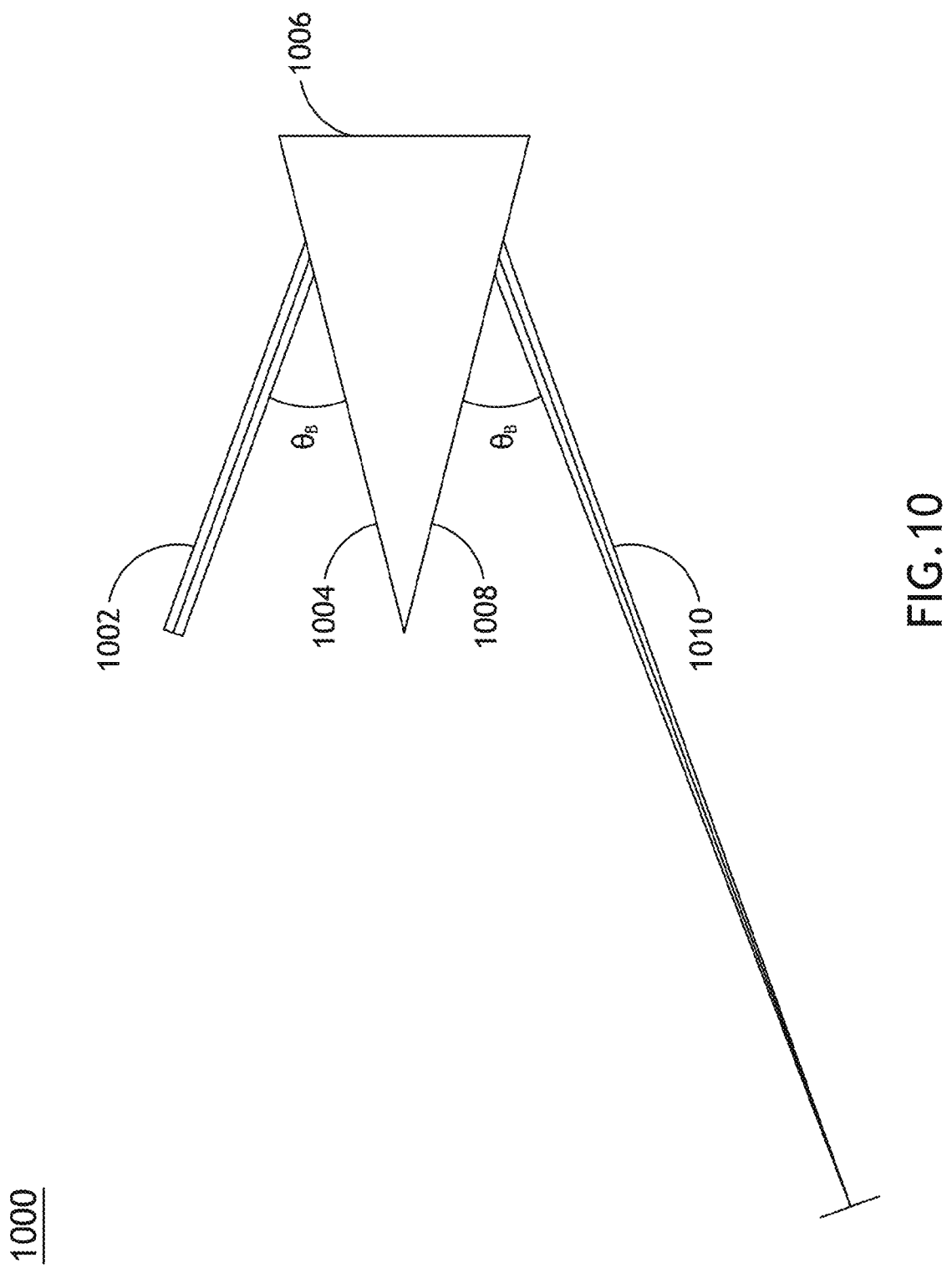
FIG. 10 illustrates a schematic diagram of a harmonic separator of the apparatus for laser frequency conversion with a high damage threshold, in accordance with an embodiment of the present invention.

FIG. 10 illustrates an alternative Brewster Angle-TIR element 1000 suitable for implementation as a harmonic separation optical element 218 of the present invention. In one aspect, the element 1000 may include one or more curved surfaces (curvature not shown) in order to provide focus the incident beam 1002. In a further embodiment, the curved surface of the element 1000 may include the TIR surface 1006 of the element 1000, allowing the element to focus light reflected from the TIR surface 1006.

It is recognized herein that the combination of the off-axis use of a focusing surface may cause astigmatism. In a further embodiment, the element 1000 may include curved surfaces at the Brewster angle surfaces 1004 and/or 1008 in order to correct for the astigmatism create by the curved TIR surface or produce a desired amount of astigmatism in the output beam 1010. In another embodiment, external Brewster angle elements (not shown) may also be utilized to fully or partially compensate for the astigmatism produced by the curved TIR 1006 surface. For example, the external Brewster angle elements used to correct the astigmatism may include one or more curved spherical or cylindrical Brewster angle surfaces.

Figure 11:
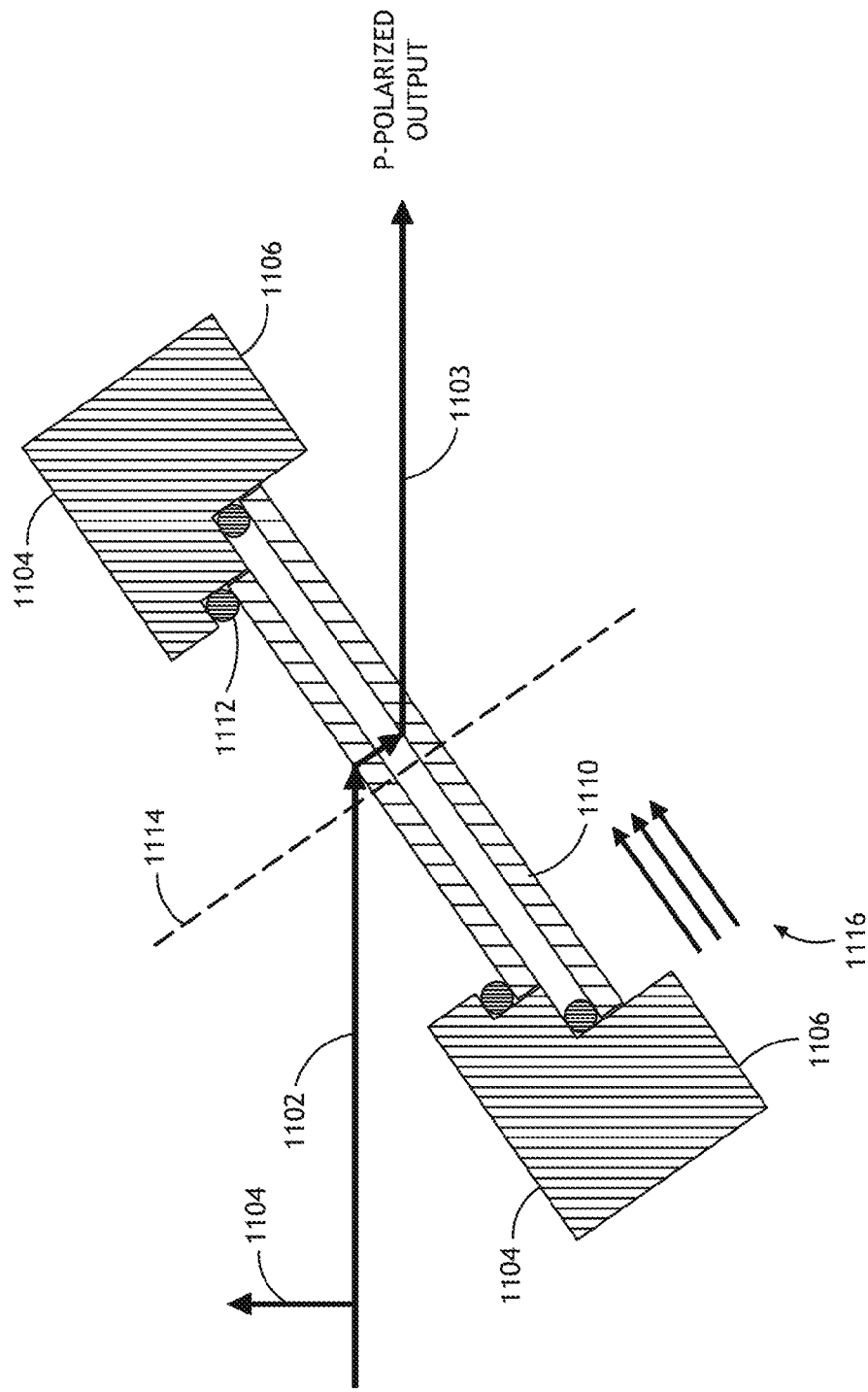
FIG. 11 illustrates a schematic diagram of a dual Brewster angle output window of the apparatus for laser frequency conversion with a high damage threshold, in accordance with an embodiment of the present invention.

FIG. 11 illustrates a dual Brewster angle window output 1100 suitable for implementation in a frequency conversion laser system, in accordance with one embodiment of the present invention. In one embodiment, the windows 1110 are oriented at Brewster's angle for the vertically polarized 11044 light 1102 exiting the enclosure 1104 of the frequency conversion system (e.g., 200 or 100), which acts to reduce or eliminate loss. It is noted herein that two windows may be utilized in order to allow for the rotation or replacement of the external window without exposing the internal portion of the laser to photocontamination. In another embodiment, the output window 1100 may include a purge system (not shown) configured to maintain laminar flow 1116 of a purging gas across the external portion of the outside window in order to limit photocontamination to this window. It is recognized herein that any suitable gas known in the art may be implemented to provide laminar flow across the external surface of the outside window of the window output 1100. For example, the purge gas may include an inert gas, such as nitrogen or argon.

In another embodiment, the Brewster angle window output 1100 may be configured to allow an emerging beam 1103 (e.g., fundamental wavelength light or alternate wavelength light) to be transmitted off-axis, that is, along a direction oriented at a non-zero angle relative to the optical axis of the optical system of the laser frequency conversion system.

In another embodiment, the windows 1110 of the dual Brewster angle window output 1100 may be fabricated utilizing any material known in the art suitable for orienting the windows at Brewster's angle for the exiting light 1102. For example, the windows 1110 may include, but are not limited to, fused silica or calcium based windows. It is recognized that the above window materials do not represent limitations, but are merely illustrative.

In an additional embodiment, the each of the windows 1110 may be sealed to the laser enclosure 1106 utilizing a seal 1112. For example, the seal 1112 may include, a low-outgassing o-ring material, such as VITON or KALRES. In another example, the seal 1112 may include a metal seal constructed from a soft metal ring, such as a metal gasket.

Figure 12:
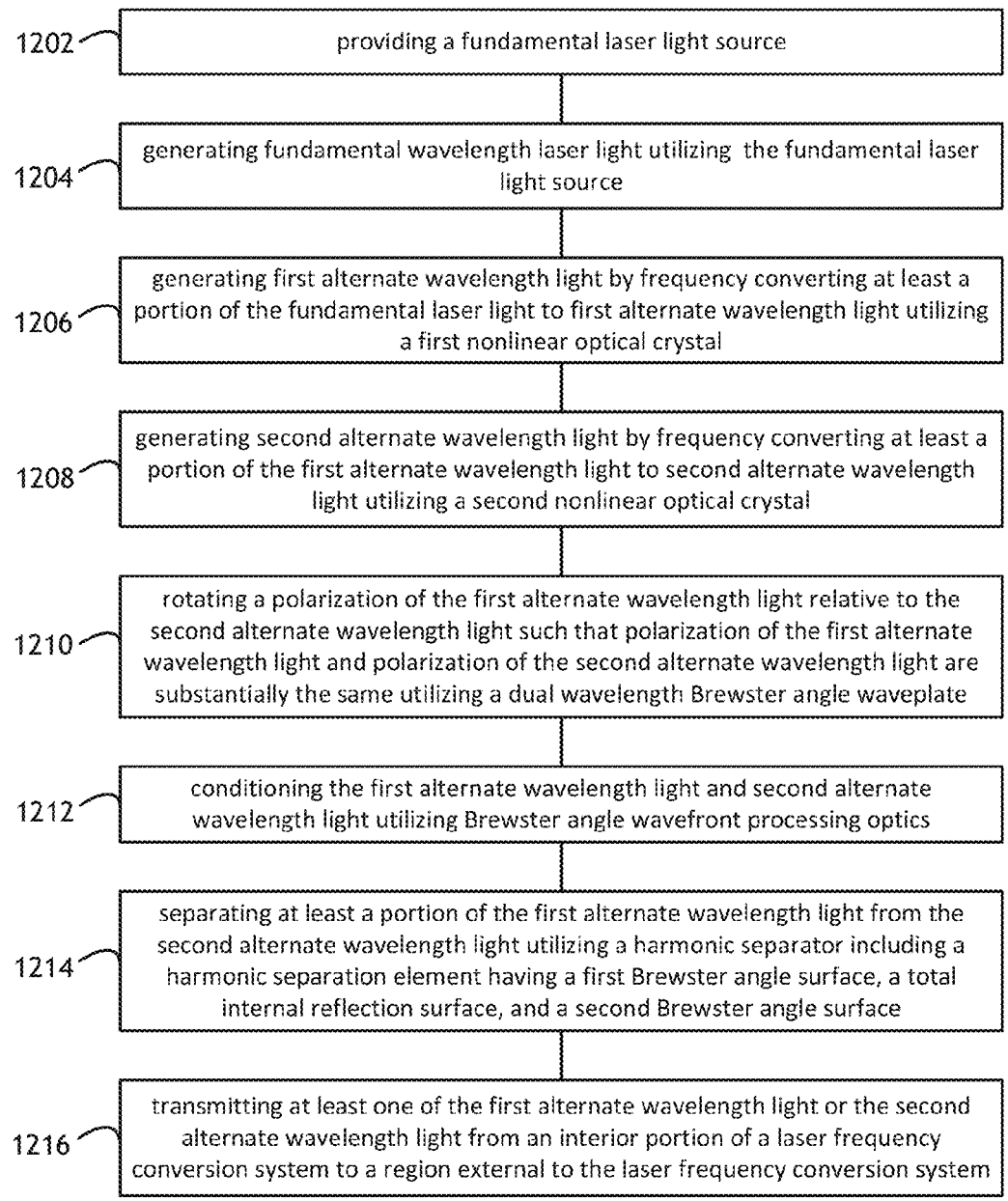
FIG. 12 illustrates a flow diagram of a method for laser frequency conversion with high damage threshold, in accordance with an embodiment of the present invention.

FIG. 12 illustrates a process flow diagram of a method 1200 for laser frequency conversion with high damage threshold, in accordance with one embodiment of the present invention. At step 1202, the method 1200 provides a fundamental laser light source. At step 1204, the method 1200 generates fundamental wavelength laser light utilizing the fundamental laser light source. At step 1206, the method 1200 generates first alternate wavelength light by frequency converting a portion of the fundamental laser light to first alternate wavelength light utilizing a first nonlinear optical crystal. At step 1208, the method 1200 generates second alternate wavelength light by frequency converting a portion of the first alternate wavelength light to second alternate wavelength light utilizing a second nonlinear optical crystal. At step 1210, utilizing a dual wavelength Brewster angle waveplate, the method 1200 rotates the polarization of the first alternate wavelength light relative to the second alternate wavelength light such that polarization of the first alternate wavelength light and polarization of the second alternate wavelength light are substantially the same. At step 1212, the method 1200 conditions (e.g., focusing, collimating, correcting astigmatism, correcting aberration) the first alternate wavelength light and the second alternate wavelength light utilizing Brewster angle wavefront processing optics. At step 1214, the method 1200 separates at least a portion of the first alternate wavelength light from the second alternate wavelength light utilizing a harmonic separator, the harmonic separator including a harmonic separation element having a first Brewster angle surface, a total internal reflection surface, and a second Brewster angle surface. At step 1216, the method 1200 transmits the first alternate wavelength light or the second alternate wavelength light from an interior portion of the laser frequency conversion system (e.g., 100 or 200) to a region external to the laser frequency conversion system.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected,"or "coupled,"to each other to achieve the desired functionality, and any two components capable of being so associated can also be viewed as being "couplable,"to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Furthermore, it is to be understood that the invention is defined by the appended claims.

What is claimed:

1. An apparatus for laser frequency conversion having a high damage threshold, comprising:
    a fundamental laser light source configured to generate fundamental wavelength laser light;
    a first nonlinear optical crystal configured to receive fundamental laser light from the fundamental laser light source, the first nonlinear optical crystal configured to generate first alternate wavelength light by frequency converting at least a portion of the received fundamental laser light to first alternate wavelength light;
    a second nonlinear optical crystal configured to receive first alternate wavelength light from the first nonlinear optical crystal, the second nonlinear optical crystal configured to generate second alternate wavelength light by frequency converting at least a portion of the received first alternate wavelength light to second alternate wavelength light;
    a set of Brewster angle wavefront processing optics configured to receive first alternate wavelength light and second alternate wavelength light from the second nonlinear optical crystal, the set of Brewster angle wavefront processing optics further configured to condition the first alternate wavelength light and second alternate wavelength light emanating from the second nonlinear optical crystal; and
    a harmonic separator configured to receive the first alternate wavelength light and the second alternate wavelength light from the set of Brewster angle wavefront processing optics, the harmonic separator configured to at least partially separate the first alternate wavelength light from the second alternate wavelength light.

2. The apparatus of claim 1, wherein the first nonlinear optical crystal is configured for second harmonic generation.

3. The apparatus of claim 1, wherein the second nonlinear optical crystal is configured for second harmonic generation.

4. The apparatus of claim 1, further comprising:
    an additional nonlinear optical crystal configured to receive second alternate wavelength light from the second nonlinear optical crystal, the additional nonlinear optical crystal configured to generate an alternate wavelength light by frequency converting at least a portion of the received second alternate wavelength light to an additional alternate wavelength light.

5. The apparatus of claim 1, further comprising:
    one or more dichroic harmonic separation elements configured to separate the fundamental light from the first alternate light, the one or more dichroic harmonic separation elements configured to direct at least a portion of the first alternate light to the second nonlinear optical crystal.

6. The apparatus of claim 1, wherein the set of Brewster angle wavefront processing optics comprises: at least one lens.

7. The apparatus of claim 6, wherein the at least one lens comprises: at least one fused silica lens or at least one calcium fluoride lens.

8. The apparatus of claim 1, wherein the set of Brewster angle wavefront processing optics comprises: a first lens and a second lens.

9. The apparatus of claim 8, wherein a surface of the first lens or a surface of the second lens comprises a cylindrical surface.

10. The apparatus of claim 8, wherein the set of Brewster angle wavefront processing optics are configured to adjust the separation between the first lens and the second lens in order to adjust for astigmatism in at least one of the first alternate wavelength light or second alternate wavelength light.

11. The apparatus of claim 1, wherein the set of Brewster angle wavefront processing optics are configured to correct for astigmatism in at least one of the first alternate wavelength light or the second alternate wavelength light.

12. The apparatus of claim 1, wherein the set of Brewster angle wavefront processing optics are configured to focus at least one of the first alternate wavelength light or the second alternate wavelength light.

13. The apparatus of claim 1, wherein the set of Brewster angle wavefront processing optics are configured to collimate at least one of the first alternate wavelength light or the second alternate wavelength light.

14. The apparatus of claim 1, wherein the set of Brewster angle wavefront processing optics are configured to correct abberative effects in at least one of the first alternate wavelength light or the second alternate wavelength light.

15. The apparatus of claim 1, wherein the harmonic separator comprises: a harmonic separation element, the harmonic separation element having a first Brewster angle surface, a total internal reflection (TIR) surface, and a second Brewster angle surface, the TIR surface between the first Brewster angle surface and the second Brewster angle surface.

16. The apparatus of claim 15, wherein the TIR surface comprises: a curved TIR surface, wherein the curved TIR surface is configured to focus light reflected from the TIR surface.

17. The apparatus of claim 15, wherein at least one of the first Brewster angle surface or the second Brewster angle surface is curved in order to compensate for aberrations produced by a curvature of the TIR surface.

18. The apparatus of claim 15, further comprising: a Brewster angle element configured to compensate for aberrations produced by a curvature of the TIR surface.

19. The apparatus of claim 15, wherein the at least one lens comprises: at least one fused silica lens or at least one calcium fluoride lens.

20. The apparatus of claim 1, wherein the harmonic separator comprises: a first harmonic separation element and a second harmonic separation element.

21. The apparatus of claim 1, wherein the harmonic separator comprises: a harmonic separation element and a Brewster angle element, the Brewster angle element configured to receive a first wavelength of light and a second wavelength of light from the first harmonic separation element.

22. An apparatus for laser frequency conversion having a high damage threshold, comprising:
    a fundamental laser light source configured to generate fundamental wavelength laser light; at least one nonlinear optical crystal configured to generate alternate wavelength light by frequency converting at least a portion of received laser light to alternate wavelength light;
    a set of Brewster angle wavefront processing optics configured to receive fundamental wavelength light and alternate wavelength light from the nonlinear optical crystal, the set of Brewster angle wavefront processing optics further configured to condition the fundamental wavelength light and the alternate wavelength light emanating from the nonlinear optical crystal; and
    a harmonic separator configured to receive fundamental wavelength light and alternate wavelength light from the set of Brewster angle wavefront processing optics, the harmonic separator configured to at least partially separate the fundamental wavelength light from the alternate wavelength light.

23. A method for laser frequency conversion with high damage threshold, comprising:
    providing a fundamental laser light source; generating fundamental wavelength laser light utilizing the fundamental laser light source;
    generating first alternate wavelength light by frequency converting at least a portion of the fundamental laser light to first alternate wavelength light utilizing a first nonlinear optical crystal;
    generating second alternate wavelength light by frequency converting at least a portion of the first alternate wavelength light to second alternate wavelength light utilizing a second nonlinear optical crystal;
    conditioning the first alternate wavelength light and second alternate wavelength light utilizing Brewster angle wavefront processing optics; and
    separating at least a portion of the first alternate wavelength light from the second alternate wavelength light utilizing a harmonic separator including a harmonic separation element having a first Brewster angle surface, a total internal reflection surface, and a second Brewster angle surface.

* * * * *